(12) United States Patent
Kuykendall

(10) Patent No.: US 8,772,576 B2
(45) Date of Patent: Jul. 8, 2014

(54) HERBICIDE-RESISTANT INOCULANT STRAINS

(76) Inventor: L. David Kuykendall, Ellicot City, MD (US)

(*) Notice: Subject to any disclaimer, the term of this patent is extended or adjusted under 35 U.S.C. 154(b) by 0 days.

(21) Appl. No.: 13/393,869

(22) PCT Filed: Sep. 3, 2010

(86) PCT No.: PCT/US2010/047817
§ 371 (c)(1),
(2), (4) Date: May 30, 2012

(87) PCT Pub. No.: WO2011/029002
PCT Pub. Date: Mar. 10, 2011

(65) Prior Publication Data
US 2012/0266332 A1    Oct. 18, 2012

Related U.S. Application Data

(60) Provisional application No. 61/239,740, filed on Sep. 3, 2009.

(51) Int. Cl.
*C12R 1/41* (2006.01)

(52) U.S. Cl.
USPC ............................................ 800/300; 435/252.2

(58) Field of Classification Search
None
See application file for complete search history.

(56) References Cited

U.S. PATENT DOCUMENTS 5,627,061 A * 5/1997 Barry et al. .................. 800/288
6,872,562 B2 * 3/2005 King et al. ................. 435/252.2

OTHER PUBLICATIONS

Sato et al, GenBank Accession No. BAC46003, Direct Submission, Submitted on Nov. 20, 2002.*

* cited by examiner

*Primary Examiner* — David H Kruse
*Assistant Examiner* — Mykola Kovalenko
(74) *Attorney, Agent, or Firm* — Standley Law Group LLP

(57) ABSTRACT

Exemplary embodiments are directed to a herbicide resistant $N_2$-fixing microorganism and to a method for enhancing $N_2$ fixation by the herbicide resistant rhizobia in symbiosis with herbicide resistant or tolerant leguminous plants treated with herbicide. At least one preferred embodiment comprises mutant rhizobia strains selected based on tolerance of the broad spectrum glyphosate weed control agent, originally Roundup®. Preferred embodiments can be expected to out-compete both indigenous soil rhizobia and/or commercial rhizobia that are not resistant to the herbicide.

5 Claims, 2 Drawing Sheets

HERBICIDE-RESISTANT INOCULANT STRAINS

CROSS-REFERENCE TO RELATED APPLICATIONS

Figure 1:
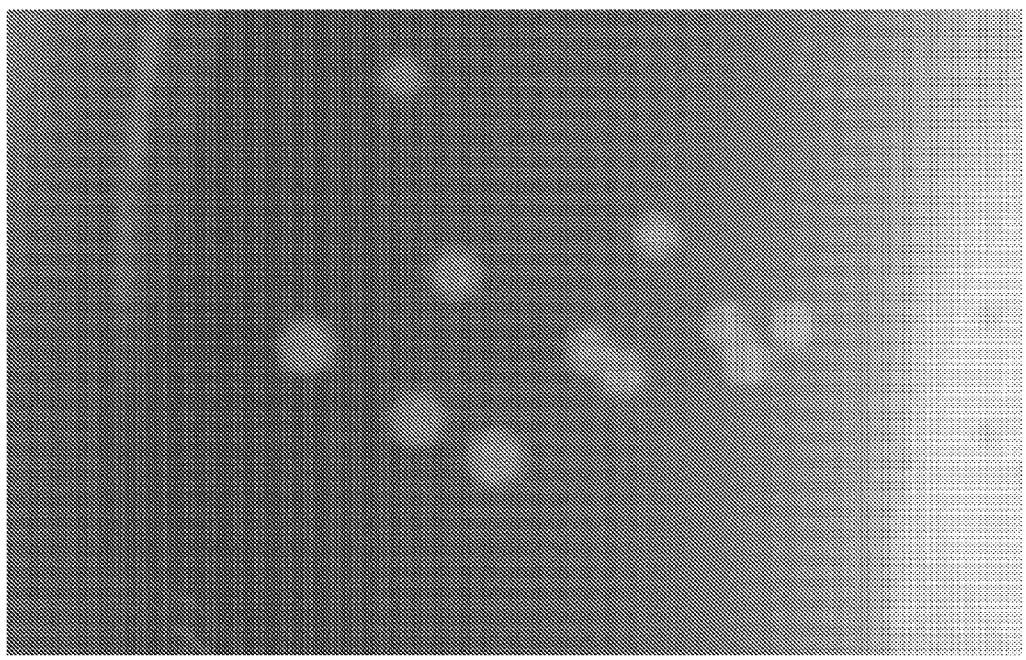

This application claims the benefit of U.S. Provisional Application No. 61/239,740, filed Sep. 3, 2009, which is herein incorporated by reference in its entirety.

TECHNICAL FIELD

Exemplary embodiments relate to improved nitrogen fixing, herbicide-resistant bacterial strains as inoculants for plants. More particularly, exemplary embodiments include dinitrogen ($N_2$) fixing, glyphosate-resistant bacteria strains belonging to the family Bradyrhizobiaceae.

BACKGROUND

Leguminous plants, such as soybean, form a symbiotic relationship with dinitrogen ($N_2$) fixing bacteria commonly called "rhizobia" that live within nodules on the roots, forming an intimate inter-kingdom association of the two organisms to reduce ("fix") dinitrogen gas in the atmosphere into a form which the plants can use as a nitrogen source. As a result, well-nodulated plants do not require extensive nitrogen fertilization. The slow-growing bacteria forming symbioses with certain legumes including soybean belong to the family Bradyrhizobiaceae. These microorganisms are a diverse group of gram-negative, nonspore-forming, rod-shaped, aerobic alpha-proteo bacteria.

Originally, rhizobia were classified as a single genus. More recent classifications, however, have placed legume-nodulating nitrogen-fixing rhizobia into six genera, belonging to a four families, within the new order Rhizobiales. These distinct taxonomic groups are based upon sequence similarities of 16S rRNA. Current taxonomic divisions of rhizobia have placed several clusters of rhizobia in four families together within the alpha-proteo bacteria based upon these sequence similarities. Among the most common genera within rhizobia are: *Rhizobium, Sinorhizobium, Azorhizobium, Mesorhizobium*, and *Bradyrhizobium*.

The bacteria infect the root, forming nodules where biological $N_2$ fixation occurs that supplies 40 to 85% of the soybean's nitrogen requirements. Nitrogen fixation commences about two-to-three weeks after the infection process begins and is indicated by large, nearly spherical yet somewhat irregularly shaped nodules having a textured surface with localized areas of pinkish red interior color due to the presence of leghemoglobin. Early in the growing season, nodules are clustered near the root crown. Later, the younger nodules located on secondary roots become more important in $N_2$ fixation activity. Nodules must be present for significant $N_2$ fixation to occur as they provide a protected ecological niche for the nitrogen-fixing bacteroids, a differentiated form of varying viability depending on the bacterial species.

Not all nodules are effective, however. Effectiveness of nodules is reflected in the ability of the bacteria within nodules to fix dinitrogen. Effective nodules are those nodules formed on legume roots that have the ability to fix (reduce) $N_2$ symbiotically at high rates relative to a recognized superior rhizobial strain which serves as a standard strain, such as strain USDA 110 for *B. japonicum* infecting soybean. Kuykendall and Elkan (1976) described the derivation of strain 110 substrains varying many fold in symbiotic nitrogen fixation ability and also differing qualitatively and/or quantitatively in ability to utilize simple 5 and 6 carbon polyols and hexose sugars.

Glyphosate [N-(phosphonomethyl)glycine] is the active ingredient in the non-selective herbicide Roundup® (Monsanto Co., St. Louis, Mo. 63167). Advances in biotechnology have resulted in glyphosate resistant or tolerant (GR) soybean cultivars, providing an effective broad-spectrum post-emergence weed-control option. Glyphosate competitively inhibits 5-enolpyruvylshikimate-3-phosphate synthase (EPSPS). Commercial glyphosate resistant or tolerant (GR) soybean expresses an EPSPS that is resistant or tolerant to glyphosate.

Glyphosate is not readily degraded in soybean and concentrates in metabolic sinks, such as young roots and developing and mature nodules. A single foliar application of glyphosate at 0.5 kg ha$^{-1}$ can result in concentrations up to 0.3 mM in bulk root tissue of susceptible plant species. Higher glyphosate use rates or repeated applications may result in even greater concentrations, especially in the stronger metabolic sinks such as soybean root nodules as compared to the bulk root system.

The use of glyphosate as a herbicidal chemical to control weeds in the cultivation of specially resistant crop plants, such as soybean, has been historically viewed as largely innocuous with regards to symbiotic nitrogen fixation in legumes including soybeans. However, detrimental effects may occur since, although EPSPS in GR soybean is resistant or tolerant to glyphosate, strains of the $N_2$ fixing microsymbionts, such as *Bradyrhizobium japonicum*, have a sensitive form of the enzyme. Researchers have concluded that glyphosate herbicide may show enough cytotoxicity, particularly to certain agronomical-elite, seed-borne inoculant rhizobia, to reduce their viability and thus lower their ability to contribute nitrogen to the planted crop (Zablotowicz and Reddy, 2004)

While applications of environmentally unwise and expensive chemical fertilizer can offset inoculation failure, this practice is not sustainable and less costly and more environmentally friendly alternatives are needed. Genetically engineered bacterial strains may carry undesirable, introduced antibiotic resistance gene(s), for example kanamycin resistance. It is therefore an unmet advantage of the prior art to provide biologically effective, herbicide resistant bacterial strains via direct mutant selection.

SUMMARY

This and other unmet advantages are provided by the embodiments and exemplary methods described and shown in more detail below.

Exemplary embodiments are directed to novel herbicide resistant rhizobia strains for enhancing the growth of plants. The microorganism of an exemplary embodiment is a mutant of a *Bradyrhizobium japonicum*, ABM strain 201. In various embodiments, the herbicide resistant microorganism retains the symbiotic effectiveness of its parent strain, however, it can grow substantially unaffected at glyophosate levels that inhibit or kill its wildtype parent strain.

An exemplary embodiment also includes an inoculant for enhancing plant growth, comprising a plant growth promoting nitrogen-fixing rhizobacteria. A preferred embodiment comprises a mutant of a nitrogen-fixing rhizobacterium of the species *Bradyrhizobium japonicum*. In various embodiments, the resistant rhizobia may be utilized as an inoculant for leguminous plants, particularly plants that are resistant or tolerant to a glyphosate containing herbicide. Exemplary embodiments are directed to herbicide resistant $N_2$-fixing rhizobia and to a method for enhancing $N_2$ fixation by the herbicide resistant rhizobia in symbiosis with herbicide resistant or tolerant leguminous plants treated with herbicide. At least one preferred embodiment comprises mutant rhizobia strains selected based on tolerance of the broad spectrum glyphosate weed control agent, originally Roundup®. Preferred embodiments can be expected to outcompete both indigenous soil rhizobia and/or commercial rhizobia that are not resistant to the herbicide.

Advantageously, various exemplary embodiments described herein do not require the incorporation of exogenous genetic material to achieve increased glyphosate tolerance. Accordingly, various embodiments may not be subject to regulatory and political hurdles caused by other methods of conferring resistance to microorganisms. With that said, embodiments disclosed herein may be genetically transformed for specific applications if desired.

An exemplary embodiment improves the practice of soybean inoculation through the use of bacterial strains developed to be highly resistant to the broad-spectrum, non-specific herbicide glyphosate. Various embodiments include isolated and purified strains identified by direct mutant selection or screening for resistance or otherwise developed as a result of direct mutant selection or screening.

An exemplary method includes using glyphosate-resistant *Bradyrhizobium* strains as seed inoculants to substantially improve nodule occupancy and consequently tightly couple the efficiency with which nitrogen sufficiency is provided soybeans by the glyphosate-resistant, genetically-improved commercial inoculant.

An exemplary embodiment shows normal growth and viability on 80 ppm glyphosate, whereas the parent strain is totally inhibited by less than 40 ppm glyphosate. Accordingly, isolated and purified embodiments of the present invention may be more than twice as tolerant of herbicide concentrations as the parent strain ABM201 or typical wildtype soil strains which are not resistant to glyphosate.

At least one exemplary embodiment relates to method of treating a plant or a plant seed with embodiments of the present invention. An exemplary method comprises the steps of providing a preparation or a formulation comprising a microorganism designated PTA-10253 (American Type Culture Collection (ATCC®), Manassas, Va., USA), and applying the preparation or the formulation to a plant or plant seed under conditions effective to treat the plant or plant seed. The application of a preferred embodiment is expected to improve nutrition and/or yield of the treated plant under herbicide treated conditions. Particularly when used in conjunction with higher glyphosate application levels and second generation glyphosate-resistant soybeans (or first generation Roundup Ready™ soybeans and the highest level of herbicide they will tolerate), exemplary embodiments should boost seed yield and improve seed quality.

The Biological Deposit

The various embodiments of the invention can be more fully understood from the following detailed description and biological deposit which forms a part of this application.

Applicants made a biological deposit under the terms of the Budapest Treaty on the International Recognition of the Deposit of Microorganisms for the Purposes of Patent Procedure. The deposit was made on Aug. 6, 2009, with the Depositor Identification Reference ABM 009 and International Depository Designation PTA 10253.

A culture of the microbe has been deposited with the American Type Culture Collection (ATCC), 10801 University Blvd., Manassas, Va. 20110-2209 USA.

THE DRAWINGS

A better understanding will be obtained from the following detailed description and the accompanying drawings in which:

FIG. 1 shows colonies formed on Vincent's YEM+80 ppm glyphosate by herbicide resistant mutants of *B. japonicum* strain ABM 201, after 12 days incubation at 30° C.

Figure 2:
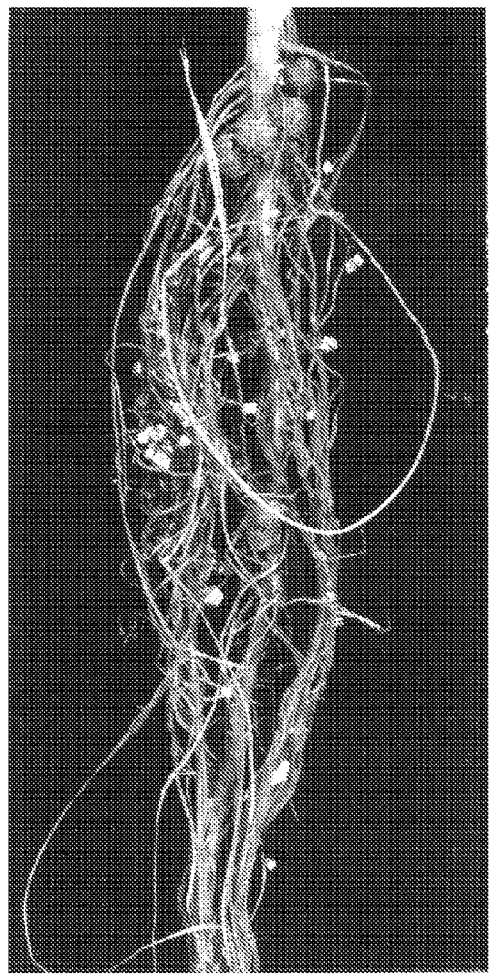

FIG. 2 shows nodules formed on soybean that had been inoculated with a highly symbiotically-effective, naturally selected glyphosate-resistant mutant strain, ATCC Accession No. PTA-10253. In the photo the nodules are formed at the crown near the top of the tap root of the soybean.

DESCRIPTION

Embodiments are directed toward herbicide resistant bacterial strains and inoculant compositions capable of enhancing the growth of plants. Embodiments also include methods for using the subject strains and inoculants. The deposit has been assigned accession number ATCC No. PTA-10253 by the repository and was deposited on Aug. 6, 2009.

Unless otherwise defined, all technical and scientific terms used herein have the same meaning as commonly understood by one of ordinary skill in the art to which this invention pertains. Although methods and materials similar or equivalent to those described herein can be used in the practice or testing of the exemplary embodiments, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The section headings used herein are for organizational purposes only and are not to be construed as limiting the described subject matter in any way. It will be appreciated that there is an implied "about" prior to metrics such as temperatures, concentrations, and times discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention. The articles "a" and "an" are used herein to refer to one or to more than one (i.e., to at least one) of the grammatical object of the article. By way of example, "an element" means one element or more than one element.

Various herbicide resistant bacteria were isolated at a rate of about one in five to ten million cells under high level glyphosate selection conditions that prevent growth of its parent strain and natural soil bacteria. An exemplary embodiment comprises a biologically pure strain of a glyphosate-resistant *Bradyrhizobium*, designated as PTA-10253, which was obtained by this direct mutant selection. Various exemplary embodiments comprise an isolated strain of bacteria, deposited as ATCC PTA-10253. In a preferred embodiment, PTA-10253 is utilized in an inoculant formulation. In various embodiments, the glyphosate resistant derivative, deposited as PTA-10253, grows unaffected at high glyphosate levels that totally inhibit or kill its wildtype parent strain.

The deposited strain is a mutant derived by direct mutant selection. In various embodiments, the subject strain may be further mutagenized or otherwise manipulated (e.g., via the introduction of a plasmid). Accordingly, embodiments include mutants, variants, and or derivatives of the strain deposited as PTA-10253, both naturally occurring and artificially induced mutants. For example, mutants may be induced by subjecting the enhancing bacteria to known mutagens, such as N-methyl-nitrosoguanidine, using conventional methods.

"Glyphosate resistance" and "Glyphosate resistant" when referring to nitrogen fixing rhizobia of exemplary embodiments refers to the ability of the bacteria to survive and reproduce following exposure to a dose of glyphosate normally inhibitory or lethal to a non-resistant rhizobia wildtype strain.

"Herbicide resistance" refers to the inherited ability of a bacteria or plant to survive and reproduce following exposure to a dose of herbicide normally inhibitory or lethal to the wildtype.

"Rhizobia" refers to members of genera *Rhizobium, Sinorhizobium, Azorhizobium, Mesorhizobium*, and most especially *Bradyrhizobium* that form symbiotic relationships with leguminous plants, including *B. japonicum, Bradyrhizobium elkanii, Sinorhizobium fredii, Sinorhizobium meliloti, Sinorhizobium* sp. NGR234, *Rhizobium leguminosarum biovar viciae, R. leguminosarum biovar trifolii, R. leguminosarum biovar phaseoli, R. tropici, R. etli, Mesorhizobium loti*, and *Azorhizobium caulinodans*.

"Inoculate" and "Inoculating" when referring to the rhizobia and leguminous plants of the present invention refer to the introduction of viable rhizobia into seed furrows at time of planting or applying the rhizobia to the seeds at a population sufficient to form effective nodules. The density of inoculation of subject bacterial cultures onto seed or into the furrows should be sufficient to populate the sub-soil region adjacent to the roots of the plant with viable bacterial growth. An effective amount of bacterial inoculant should be used. An effective amount is that amount sufficient to establish sufficient bacterial growth so that the yield from the plant is increased.

As used herein, reference to "isolated" means that the subject strain is removed from the environment in which the wildtype strain normally exists in nature. Thus, the isolated strain may exist as, for example, a biologically pure culture in association with an agricultural carrier. As may be readily appreciated by one of skill in the art, the mutant strain deposited as PTA-10253 is not known to exist in nature.

As used herein, the term "increasing plant growth" or "enhancing plant growth" includes, without limitation, increasing plant weight, increasing nodule number, increasing nodule weight, increasing nitrogen fixation, increasing total biomass, and or increasing grain yield.

In various embodiments, bacteria can be combined with an inert carrier to form a composition suitable for applying to soil or a plant material. In various embodiments, ATCC Accession No. PTA-10253 can be used as a solid. For example, a culture of ATCC Accession No. PTA-10253 may be grown in a suitable growth medium, the bacteria separated from the spent medium, resuspended in a fresh medium and the bacteria spray-dried. The resulting powder can be used. Alternatively, ATCC Accession No. PTA-10253 can be used as a liquid, e.g., a culture of ATCC Accession No. PTA-10253 can be grown in a suitable growth medium, the bacteria separated from the spent medium, and resuspended in water, buffer or fresh medium. The resulting suspension can be used.

In other embodiments, the bacterial strain designated as ATCC Accession No. PTA-10253 can be combined with one or more compounds to form a mixture suitable for packaging or applying the bacteria to seed. Compounds that can be combined with the bacterial strain designated as PTA-10253 include fertilizers, micronutrient donors, surfactants, or adjuvants conventionally employed in the art of formulation. The number of compounds selected for a given mixture may be chosen in accordance with the intended application and/or existing conditions. The resulting mixture can be a solid or a liquid, e.g., an emulsifiable concentrate, a coatable paste, a directly sprayable solution, a dilutable solution, a dilute emulsion, a wettable powder, a dusting powder, a granular formulation, or an encapsulated formulation. In some embodiments, a growth medium is also included in the composition. In various embodiments, an amount of water is present in the composition. For liquid concentrates, water is up to 99% by weight.

PCT Publication No. WO2007/030557 (U.S. patent application Ser. No. 11/517,051) and U.S. Patent Pub. No. US2009/0048128 (U.S. patent application Ser. No. 12/119, 178), fully incorporated by reference in their entirety, disclose various formulations for microorganisms. Those applications also disclose methods for producing and utilizing various formulations. The herbicide resistant microorganisms of exemplary embodiments described herein may be utilized in conjunction with the compositions and or methods described in application Ser. Nos. 11/517,051 and 12/119, 178, particularly those directed toward encapsulating microorganisms, along with other substances to produce new and useful formulations and methods. For example, embodiments include an inoculant formulation of viable microorganisms comprising an effective amount of the microorganism deposited as PTA-10253 along with an encapsulating material that forms microbeads encapsulating the microorganism deposited as PTA-10253. In at least one embodiment, the encapsulating material is a water soluble material capable of forming microbeads containing the microorganism deposited as PTA-10253 when dried. Suitable encapsulating materials include, without limitation, native or modified chitosans, native of modified starches, glucans or dextrins, celluloses modified so they are soluble, and any of a number of native or modified vegetable or microbial gums, including agars, guar, locust, carrageenan, xanthans, pectins, and the like, and combinations thereof. In a preferred embodiment, the encapsulating material is a dextrin, such as Crystal-Tex (National Starch and Chemical Co., Bridgewater, N.J.). Encapsulating the microorganisms pursuant to the method of the present invention provides many advantages. In particular, encapsulated microorganisms are more resistant to chemical pesticides, which may dramatically reduce the shelf life of unencapsulated microorganisms by contact toxicity.

In at least one embodiment, the formulation may comprise a herbicide resistant microorganism deposited as PTA-10253 in an amount of at least $5 \times 10^8$ colony forming units per gram of the formulation; an encapsulating material that forms microbeads encapsulating the microorganisms when dried; and a water insoluble, water-absorbent substance mixed with the microorganisms, the water insoluble, water-absorbent substance present in an amount sufficient to maintain the formulation as a dry, free-flowing powder. In some embodiments, the inoculant composition further comprises a particulate machine lubricant including at least one of talc and graphite.

Exemplary embodiments described herein may specifically improve the efficacy of such seed inoculant formulations, especially when used in the presence of glyphosate.

Embodiments also feature methods comprising applying a composition to improve nutrition and/or yield of the treated plant under herbicide treated conditions. Such an environment can be soil, a plant seed, a plant, or a plant part (e.g., leaves and stems). The composition typically is applied in an amount effective to provide nitrogen sufficiency in the treated plant. Typically, the rate of application is about $1.3 \times 10^3$ cfu/$cm^2$ to about $1.3 \times 10^8$ cfu/$cm^2$ of soil or seed, or about $1.3 \times 10^3$ cfu to about $1.3 \times 10^8$ cfu per seed or cutting. Like the nature of the composition, a method of application such as spraying, atomizing, dusting, scattering or pouring, is chosen in accordance with the intended objectives and the prevailing circumstances.

Particularly suitable methods for applying a composition include methods that involve seed coating, soil application or incorporation into a growth medium. The number of times that a composition is applied may vary depending on the application. A composition can be applied to soil as a liquid, but can also be applied to soil in granular form. Outdoor soil applications can be in furrow, broadcast, or soil injection. In greenhouse or other indoor environments, a composition can be applied by mixing with potting soils typically used in such environments. A composition may also be applied to seeds by impregnating the seeds with a liquid formulation, or coating them with a solid formulation. In various embodiments, liquid suspensions of bacteria (in water or a growth media) may be applied to seed at a rate of 5 to 10 ml per kg of seed and allowed to dry prior to bagging and storage. In special cases, further types of application are also possible, for example, selective treatment of individual plant stems or buds.

The methods and compositions of the invention may be useful for increasing growth in a wide range of plants, including, without limitation, legumes, non-legumes, cereals, oilseeds, fiber crops, starch crops and vegetables. Non-limiting examples of legumes include soybeans; peanuts; chickpeas; all the pulses, including peas and lentils; all the beans; major forage crops, such as alfalfa and clover; and many more plants of lesser agricultural importance, such as lupines, sainfoin, trefoil, and even some small tree species. Non-limiting examples of cereals include corn, wheat, barley, oats, rye and triticale. Non-limiting examples of oilseeds include canola and flax. Non-limiting examples of fiber crops include hemp and cotton. Non-limiting examples of starch crops include potato, sugar cane and sugar beets. Non-limiting examples of vegetables include carrots, radishes, cauliflower, broccoli, peppers, lettuce, cabbage, peppers, celery and Brussels sprouts.

Techniques for applying inoculants to plants are known in the art, including appropriate modes of administration, frequency of administration, dosages, et cetera. Typically, inoculants are in a liquid or powdered form. Suitable auxiliaries, such as carriers, diluents, excipients, and adjuvants are known in the art. For example, dry or semi-dry powdered inoculants often comprise the microorganism(s) of interested dispersed on powdered peat, clay, other plant material, or a protein such as casein. The inoculant may include or be applied in concert with other standard agricultural auxiliaries such as fertilizers, pesticides, or other beneficial microorganisms.

The inoculant may be applied to the soil prior to, contemporaneously with, or after sowing seeds, after planting, or after plants have emerged from the ground. The inoculant may also be applied to seeds themselves prior to or at the time of planting (e.g. packaged seed may be sold with the inoculant already applied). The inoculant may also be applied to the plant after it has emerged from the ground, or to the leaves, stems, roots, or other parts of the plant.

Inoculants of the various embodiments may contain only one plant growth promoting bacterial strain (e.g., the microorganism deposited as PTA-10253) or may contain combinations of different bacterial strains. One or more strains of nitrogen-fixing rhizobacteria or other beneficial microorganisms may also be present.

Kits containing an inoculant will typically include one or more containers of the inoculant, and printed instructions for using the inoculant for promoting plant growth. The kit may also include tools or instruments for reconstituting, measuring, mixing, or applying the inoculant, and will vary in accordance with the particular formulation and intended use of the inoculant.

Further details concerning the preparation of bacterial inoculants and methods for inoculating plants with bacterial inoculants are found in e.g. U.S. Pat. Nos. 5,586,411; 5,697,186; 5,484,464; 5,906,929; 5,288,296; 4,875,921; 4,828,600; 5,951,978; 5,183,759; 5,041,383; 6,077,505; 5,916,029; 5,360,606; 5,292,507; 5,229,114; 4,421,544; and 4,367,609, each of which is incorporated herein by reference.

Accordingly, the following embodiments include:

An isolated microorganism deposited as ATCC accession number, PTA-10253, or a herbicide resistant strain derived therefrom.

In some embodiments, the microorganism is a *Bradyrhizobium* deposited as ATCC accession number, PTA-10253.

In various embodiments, the microorganism does not contain an artificial exogenous nucleic acid (e.g., a plasmid).

In various embodiments, the microorganism is glyphosate resistant. In some embodiments, the microorganism exhibits normal growth and viability at a glyphosate concentration between about 40 ppm to at least about 80 ppm glyphosate. In other embodiments, the microorganism exhibits normal growth and viability at a glyphosate concentration between about 50 ppm at least about 80 ppm glyphosate. In still other embodiments, the microorganism exhibits normal growth and viability at a glypho sate concentration between about 60 ppm to at least about 80 ppm glyphosate. In yet other embodiments, the microorganism exhibits normal growth and viability at a glyphosate concentration between about 70 ppm to at least about 80 ppm glyphosate. In still other embodiments, the microorganism exhibits normal growth and viability at a glyphosate concentration of about 80 ppm.

At least on embodiment comprises an isolated culture comprising the microorganism deposited as ATCC accession number, PTA-10253, or a strain derived therefrom.

Embodiments further include an inoculant for application to plants, comprising an effective quantity of the microorganism deposited as ATCC accession number, PTA-10253, or a strain derived therefrom, and an agricultural carrier. In some embodiments, the carrier is a seed treatment. In various embodiments, the carrier is a liquid. In other embodiments, the carrier is a solid.

In various embodiments, the effective quantity of the microorganism comprises an amount of at least $5 \times 10^8$ colony forming units per gram of the formulation; and the inoculant further comprises an encapsulating material that forms microbeads encapsulating the herbicide resistant rhizobia strain when dried. In some embodiments, the inoculant composition comprises a particulate machine lubricant including at least one of talc and graphite.

Embodiments include a method for enhancing the growth of a plant, the method comprising the step of placing in the vicinity of the plant an effective quantity of a herbicide resistant microorganism deposited as ATCC accession number, PTA-10253 or a strain derived therefrom, the strain able to enhance the growth of plants. Various embodiments further comprises the step of administering the herbicide resistant microorganism by a method selected from the group consisting of application to the seeds of the plant, application to the plant, application to the locus of the plant root, and application by in-furrow spray.

In some embodiments, the method further comprises the step of applying a glyphosate-containing herbicide to the plant. In various embodiments, the applying step is performed by a method selected from the group consisting of application before administering the herbicide resistant microorganism, application simultaneously with administering the herbicide resistant microorganism, and application after administering the herbicide resistant microorganism.

In exemplary embodiments, the plant is a legume. In specific embodiments, the legume is a soybean plant. In various embodiments, the plant is a glyphosate-resistant soybean plant.

Embodiments further include a glyphosate-resistant soybean plant infected by a herbicide resistant microorganism deposited as ATCC accession number, PTA-10253 or a strain derived therefrom

EXAMPLES

Exemplary embodiments are further detailed in the following examples, which are offered by way of illustration and are not intended to limit the invention in any manner.

Example 1

Isolation and Purification of Derivative, Herbicide Resistant Microorganisms

Direct mutant selections were performed within Petri dishes poured with Vincent's yeast extract, +D-mannitol agar (Vincent, 1970) amended with high level glyphosate. Approximately 25 mL agar plates were initially spread with 100 μL of an undiluted commercial glyphosate formula (Roundup®) containing 2% glyphosate, resulting in a plate concentration of 80 ppm glyphosate. After the plates were sufficiently dry, about $10^8$ to $5 \times 10^8$ colony-forming units (CFU) of the parent bacteria (ABM201) (Advanced Biological Marketing, Van Wert, Ohio), determined by serial dilution and plating on nonselective medium, were spread with a sterile, bent glass rod. The plates were carefully wrapped with Parafilm® to prevent the desiccation of the agar growth medium during prolonged incubation. The plates were then incubated at room temperature to 30° C. for approximately 2 to 3 weeks.

Colonies that developed resembled the parent strain and its growth characteristics on non-selective YEM medium. The colonies were convex, entirely opaque, smooth, and only about 1 mm in diameter after 10-14 days of incubation. Mutant frequency was about $5 \times 10^{-7}$ to $1 \times 10^{-6}$. FIG. 1 shows a photograph of glyphosate-resistant mutant bacterial colonies from successful direct selection of glyphosate-resistant *Bradyrhizobium* strain 201. Mutant glyphosate-resistant bacterial colonies were picked with a sterile inoculating loop and then streaked on glyphosate medium of the same composition as selection, for purification.

Example 2

Nodulation Testing of Herbicide Resistant Microorganisms

In order to determine whether the derivative microorganisms were biologically effective, a nodulation test in vermiculite support medium with nitrogen-free Hoagland's 1950 formulation of plant nutrient solution was initiated. Briefly, Soybean seeds of the MiniMax variety (B. F. Matthews, Reg. No. CV-489, PI 643148) were surface-sterilized with 70% ethanol for 30 seconds followed by two rinses with bacteria-free water. The seeds were then inoculated with $10^7$ CFU of strain PTA-10253. After inoculation, the seeds were subjected to a photoperiod of 16 hr using a 55-watt daylight compact fluorescent bulb illuminated at a distance of about 20 cm.

As shown in FIG. 2, nodules formed near the top of the tap root of soybean inoculated with the symbiotically-effective, glyphosate-resistant mutant strain PTA-10253. The distribution and size of the nodules was similar to the parent strain and suggests the nodules are biologically effective.

Example 3

Confirmation of Nodule Occupancy of Glyphosate-resistant *Bradyrhizobium* Mutant Strain Successful direct selection of glyphosate-resistant derivatives of a parent *Bradyrhizobium* strain, ABM strain 201, one of the strains in various multi-strain soybean inoculant formulations made by ABM, was confirmed by plant passage and demonstrated recovery of glyphosate bradyrhizobia from nodules. Briefly, Petri plates poured with YEM amended with glyphosate were made as described above.

Isolation of glyphosate resistant mutants was demonstrated from nodules that had been surface-sterilized with commercial 3% hydrogen peroxide for 1 hr, followed by 3 or 4 sterile water rinses. Sterile blunt-ended glass rods were utilized as nodule-squashing instruments to re-isolate the nodule bacteria. The isolated bacteria were plated on glyphosate medium to verify resistance. Glyphosate resistant bradyrhizobia strain ABM201 mutants were obtained from nodules grown on glyphosate medium. Accordingly, these experiments successfully demonstrated that bacteria occupying the nodules in FIG. 2 were the glyphosate-resistant *Bradyrhizobium* mutant strain.

To further confirm the efficacy of ATCC strain PTA-10253, a multi-liter broth culture of PTA-10253 was prepared. A randomized block design in at least two field locations will be used to test the ability of strain PTA-10253 to boost soybean seed yield when high-level glyphosate resistant soybeans are planted and dosed with higher levels of Roundup® than traditionally employed. Strain PTA-10253 will be compared specifically with its parent strain ABM201.

References:

The following references and others cited herein but not listed here, to the extent that they provide exemplary procedural and other details supplementary to those set forth herein, are specifically incorporated herein by reference. The citation of any publication is solely for its disclosure and should not be construed as an admission that the present invention is not entitled to antedate such publication by virtue of prior invention.

B. E. Caldwell and G. Vest (1970), Effects of *Rhizobium japonicum* Strains on Soybean Yields *Crop Sci.;* 10: 19-21.

Hoagland, D. R. & Amon, D. I. (1950). The water culture method for growing plants without soil. California Agricultural Experimental Station Circular No. 347, pp. 1-32. University of California, Berkeley.

Kuykendall L D, Elkan G H (1976). *Rhizobium japonicum* derivatives differing in nitrogen-fixing efficiency and carbohydrate utilization. Appl Environ Microbiol. October;32(4):511-519.

Holt et al., in Bergey's Manual of Determinative Bacteriology, 9th Ed., Williams and Wilkins, Baltimore, Md. (1994).

Kuykendall, L. D., Young, J. M., Martinez-Romero, E., Kerr, A. and Sawada, H. 2005. Order Rhizobiales (new) Family Rhizobiaceae Genus *Rhizobium*. In Brenner, Krieg, Staley and Garrity (Eds), *The Alpha-, Beta-, Delta- and Epsilonproteobacteria, The Proteobacteria, Part C, Bergey's Manual of Systematic Bacteriology*, $2^{nd}$. Ed., Vol. 2, Springer, New York, N.Y., pp. 324-340.

Kuykendall, L. D. and Dazzo, F. B. 2005. *Allorhizobium*. In Brenner, Krieg, Staley and Garrity (Editors), *The Alpha-, Beta-, Delta- and Epsilonproteobacteria, The Proteobacteria, Part C, Bergey's Manual of Systematic Bacteriology*, $2^{nd}$. Ed., Vol. 2, Springer, New York, N.Y., pp. 345-346.

Kuykendall, L. D., Hashem, F. M. and Wang, E. T. 2005. Genus *Sinorhizobium*. In Brenner, Krieg, Staley and Garrity (Eds), *The Alpha-, Beta-, Delta- and Epsilonproteobacteria, The Proteobacteria, Part C, Bergey's Manual of Systematic Bacteriology*, $2^{nd}$. Ed., Vol. 2, Springer, New York, N.Y., pp. 358-361

Chen, W. X., Wang, E. T. and Kuykendall, L. D. 2005. Genus *Mesorhizobium*. In Brenner, Krieg, Staley and Garrity (Eds), *The Alpha-, Beta-, Delta- and Epsilonproteobacteria, The Proteobacteria, Part C, Bergey's Manual of Systematic Bacteriology*, $2^{nd}$. Ed., Vol. 2, Springer, New York, N.Y., pp. 403-408.

Kuykendall, L. D. 2005. Genus *Bradyrhizobium*. In Brenner, Krieg, Staley and Garrity (Editors), *The Alpha-, Beta-, Delta- and Epsilonproteobacteria, The Proteobacteria, Part C, Bergey's Manual of Systematic Bacteriology*, $2^{nd}$. Ed., Vol. 2, Springer, New York, N.Y., pp. 438-443.

Kuykendall, L. D. 2005 Genus *Azorhizobium*. In Brenner, Krieg, Staley and Garrity (Editors), The Alpha-, Beta-, Delta- and Epsilonproteobacteria, The Proteobacteria, Part C, Bergey's Manual of Systematic Bacteriology, $2^{nd}$. Ed., Vol. 2, Springer, New York, N.Y., pp. 505-506.

Zablotowicz, R. M., and K. N. Reddy. 2004 Impact of Glyphosate on the *Bradyrhizobium japonicum symbiosis* with glyphosate-resistant transgenic soybean: A Minireview. J. Environmental Quality 33: 825-831.

Other Embodiments

It is to be understood that while the embodiments have been described in conjunction with the detailed description thereof, the foregoing description is intended to illustrate and not limit the scope of the invention. Other aspects, advantages, and modifications are within the scope of the following claims.

What is claimed is:

1. A method for enhancing the growth of a plant, the method comprising the step of administering an effective quantity of a glyphosate resistant microorganism, of the genus *Bradyrhizobium*, deposited as ATCC accession number PTA-10253 to the plant or in the vicinity of the plant.

2. The method of claim 1, wherein:
   the step of administering the microorganism is achieved by at least one of the following:
   applying the microorganism to the seeds of the plant;
   applying the microorganism to the plant;
   applying the microorganism to the locus of the plant root; and
   applying the microorganism by in-furrow spray.

3. The method of claim 2, further comprising the step of applying a glyphosate-containing herbicide to the plant.

4. The method of claim 1, wherein the plant is a legume, resistant to glyphosate.

5. The method of claim 4, wherein the legume is a soybean plant.

* * * * *